United States Patent
Yamaguchi

(10) Patent No.: US 12,390,415 B2
(45) Date of Patent: Aug. 19, 2025

(54) METHOD FOR IMPROVING STORAGE STABILITY

(71) Applicant: SEIKAGAKU CORPORATION, Tokyo (JP)

(72) Inventor: Iwao Yamaguchi, Tokyo (JP)

(73) Assignee: SEIKAGAKU CORPORATION, Tokyo (JP)

(*) Notice: Subject to any disclaimer, the term of this patent is extended or adjusted under 35 U.S.C. 154(b) by 1046 days.

(21) Appl. No.: 17/428,425

(22) PCT Filed: Feb. 21, 2020

(86) PCT No.: PCT/JP2020/007115
§ 371 (c)(1),
(2) Date: Aug. 4, 2021

(87) PCT Pub. No.: WO2020/171212
PCT Pub. Date: Aug. 27, 2020

(65) Prior Publication Data
US 2022/0105028 A1    Apr. 7, 2022

(30) Foreign Application Priority Data
Feb. 22, 2019 (JP) ................ 2019-030416

(51) Int. Cl.
| | | |
|---|---|---|
| A61K 9/08 | (2006.01) | |
| A61B 17/3205 | (2006.01) | |
| A61K 9/00 | (2006.01) | |
| A61K 31/728 | (2006.01) | |
| A61K 47/20 | (2006.01) | |
| A61K 47/22 | (2006.01) | |
| A61B 17/00 | (2006.01) | |

(52) U.S. Cl.
CPC ...... *A61K 9/0019* (2013.01); *A61B 17/32056* (2013.01); *A61K 9/08* (2013.01); *A61K 31/728* (2013.01); *A61K 47/20* (2013.01); *A61K 47/22* (2013.01); *A61B 2017/00269* (2013.01); *A61B 2017/00681* (2013.01); *A61B 2017/00898* (2013.01)

(58) Field of Classification Search
None
See application file for complete search history.

(56) References Cited

U.S. PATENT DOCUMENTS

| | | | |
|---|---|---|---|
| 6,319,260 B1 | 11/2001 | Yamamoto | |
| 7,748,388 B2 | 7/2010 | Yamamoto | |
| 2003/0105061 A1 | 6/2003 | Ishikawa et al. | |
| 2006/0105991 A1 | 5/2006 | Ishikawa et al. | |
| 2015/0099928 A1 | 4/2015 | Smith et al. | |
| 2016/0228140 A1 | 8/2016 | Strauss et al. | |
| 2016/0317701 A1 | 11/2016 | Vogel | |
| 2017/0119661 A1 | 5/2017 | Smith et al. | |
| 2018/0021252 A1 | 1/2018 | Delaney et al. | |
| 2019/0336411 A1* | 11/2019 | Kim ................ A61K 9/0021 | |

FOREIGN PATENT DOCUMENTS

| | | | |
|---|---|---|---|
| CN | 104689381 A | 6/2015 | |
| CN | 105561402 A | 5/2016 | |
| CN | 106456789 A | 2/2017 | |
| CN | 107456612 A | 12/2017 | |
| EP | 3 400 930 A1 | 11/2018 | |
| JP | 10-194988 A | 7/1998 | |
| JP | 10-194998 A | 7/1998 | |
| JP | 2001-192336 A | 7/2001 | |
| JP | 2003-201257 A | 7/2003 | |
| WO | WO-2018134621 A1 * | 7/2018 | ............. A61B 10/04 |

OTHER PUBLICATIONS

Yoshida et al., "Efficacy of hyaluronic acid in endoscopic mucosal resection of colorectal tumors", Journal of Gastroenterology and Hepatology, 2011, vol. 26, pp. 286-291 (6 pages total).

Yoshida et al., "Endoscopic mucosal resection with 0.13% hyaluronic acid solution for colorectal polyps less than 20 mm: A randomized controlled trial", Journal of Gastroenterology and Hepatology, 2012, vol. 27, pp. 1377-1383 (7 pages total).

International Preliminary Report on Patentability (with translation of Written Opinion) dated Aug. 10, 2021, issued by the International Bureau in application No. PCT/JP2020/007115.

The package insert of MucoUp (registered trademark); pp. 1-4; Revised: Nov. 2017 (7th edition, Revised on the basis of amendment of instructions for package inserts of medical devices.); Approval No. 21800BZZ10124000.

Vitor Arantes, et al., Standardized endoscopic submucosal tunnel dissection for management of early esophageal tumors (with video), Case Study, Gastrointestinal Endoscopy, 2013, vol. 78, No. 6, www.giejournal.org, pp. 946-952.

International Search Report for PCT/JP2020/007115 dated Apr. 28, 2020.

* cited by examiner

*Primary Examiner* — Traviss C McIntosh, III
(74) *Attorney, Agent, or Firm* — Sughrue Mion, PLLC

(57) ABSTRACT

A submucosal injection material whose quality deterioration during a storage period is prevented is provided. It is a submucosal injection material, which contains hyaluronic acid, and to which a dye is added.

16 Claims, No Drawings

METHOD FOR IMPROVING STORAGE STABILITY

CROSS REFERENCE TO RELATED APPLICATIONS

This application is a National Stage of International Application No. PCT/JP2020/007115 filed Feb. 21, 2020, claiming priority based on Japanese Patent Application No. 2019-030416 filed Feb. 22, 2019.

TECHNICAL FIELD

A technique according to the present invention relates to a method for improving the storage stability of a hyaluronic acid-containing composition.

BACKGROUND ART

Endoscopic mucosal resection (hereinafter also simply referred to as EMR) is a method of resecting a mucosal lesion in the digestive tract or the like by an operation using an endoscope without performing a laparotomy, and is carried out by excising the mucosal lesion site with a snare or the like under an endoscope. For the purpose of enhancing the efficiency of this operation, improving operability and safety, or the like, a method of injecting a solution of a high-molecular polymer into a layer beneath a mucosal lesion to swell and elevate the mucosal lesion site is known. A viscous solution containing hyaluronic acid as a high-molecular polymer is used as a submucosal injection material in EMR or endoscopic submucosal dissection (hereinafter, also simply referred to as ESD).

In order to improve the notice ability of a mucosal lesion in EMR, BSD, or the like, a method of adding a dye to a solution of a high-molecular polymer to be injected for coloring has been attempted. For example, JP-A-2001-192336 describes an invention relating to a medical composition that can be used in EMR or the like containing a polysaccharide such as hyaluronic acid. JP-A-2001-192336 describes an invention relating to an injection in which sodium hyaluronate, indigo carmine, and epinephrine are enclosed in an injection container, and EMR using the injection. WO 2018/134621 describes a composition for assisting polyp removal in the form of a submucosal injection material which contains one or more salts of hyaluronic acid, physiological saline, and indigo carmine, and does not contain a substance exhibiting a vasoconstrictive effect such as epinephrine. The package insert of MucoUp (registered trademark) describes a submucosal injection material that can be used in EMR and BSD.

SUMMARY OF INVENTION

Technical Problem

It is important to provide a hyaluronic acid-containing composition whose quality deterioration during a storage period is prevented from the viewpoint of contribution to medical care.

Solution to Problem

The present inventors found that the above object is achieved by adding a dye to a hyaluronic acid-containing composition, and thus completed the present invention.

One aspect of the present invention is a method for improving the storage stability of a hyaluronic acid-containing composition including adding a dye to the composition.

Advantageous Effects of Invention

According to the present invention, a hyaluronic acid-containing composition having excellent quality retention during a storage period can be provided.

DESCRIPTION OF EMBODIMENTS

The present invention is at least partially based on the surprising finding that the addition of a small amount of a dye improves the quality retention (for example, prevention of reduction of viscosity) during a storage period of a hyaluronic acid-containing composition.

One aspect of the present invention relates to a method for improving the storage stability of a submucosal injection material containing hyaluronic acid, including adding a dye to the submucosal injection material.

Another aspect of the present invention relates to a method for preventing shortening of the shelf life of a submucosal injection material containing hyaluronic acid, including adding a dye to the submucosal injection material.

Another aspect of the present invention relates to a method for enhancing the viscosity of a submucosal injection material containing hyaluronic acid, including adding a dye to the submucosal injection material.

Another aspect of the present invention relates to a method for preventing formation of insoluble microparticles of a submucosal injection material containing hyaluronic acid, including adding a dye to the submucosal injection material.

Another aspect of the present invention relates to a submucosal injection material which contains hyaluronic acid and a dye and has improved storage stability.

Another aspect, of the present invention relates to use of a dye in the improvement of the storage stability of a submucosal, injection material containing hyaluronic acid.

Another aspect of the present invention relates to use of a dye in the production of a submucosal injection material which contains hyaluronic acid and has improved storage stability.

In the present description, when a plurality of substances corresponding to each component are present in the composition, the content of each component in the composition means the total amount of the plurality of substances present in the composition unless otherwise stated. Hereinafter, embodiments of the present invention will be described, but the present invention is not limited only to the following embodiments.

One embodiment of the present invention relates to a composition which contains hyaluronic acid and a dye and has improved storage stability. In the composition, the storage stability is improved as compared with a control which contains hyaluronic acid, but does not contain a dye. In one embodiment, for example, a submucosal injection material formed by adding a dye to a composition containing hyaluronic acid is provided, which will be described below as an example.

In the present description, "hyaluronic acid" is construed as a meaning including hyaluronic acid and a medically acceptable salt thereof. In a preferred embodiment, sodium hyaluronate is adopted as hyaluronic acid. The origin of hyaluronic acid is not particularly limited, and for example, one isolated and purified from a cockscomb, an umbilical cord, a microorganism which produces hyaluronic acid, or the like can be used.

In the present description, as the "medically acceptable salt", for example, salts with inorganic bases such as alkali metal salts (such as a sodium salt, a lithium salt, and a potassium salt), alkaline earth metal salts (such as a calcium salt), a magnesium salt, and an ammonium salt, or salts with organic bases such as a diethanolamine salt, a cyclohexylamine salt, and an amino acid salt, and the like can be exemplified, but it is not limited thereto.

The weight average molecular weight of hyaluronic acid is not particularly limited. For example, the weight average molecular weight of hyaluronic acid may be from 500,000 to 1,200,000. The weight average molecular weight of hyaluronic acid can be calculated according to the equation of Laurent et al. (Biochim. Biophys. Acta, 42, 476 (1960)) after measuring the intrinsic viscosity according to the Japanese Pharmacopoeia 13th Edition: General Test Method/Viscosity Measurement Method.

The content of hyaluronic acid in the submucosal injection material is, for example, 0.01% (w/v) or more and 5% (w/v) or less. In one preferred embodiment, the content of hyaluronic acid in the submucosal injection material is 0.1% (w/v) or more and 0.5% (w/v) or less. In a more preferred embodiment, the content of hyaluronic acid in the submucosal injection material is about: 0.4% (w/v). The submucosal injection material may contain a solvent, for example, water.

The dye used in the present invention is not particularly limited as long as it is a medically acceptable dye (colorant). As the dye, for example, indigo carmine, methylene blue, brilliant blue, trypan blue, evans blue, toluidine blue, phenol red, congo red, and the like can be exemplified. In a preferred embodiment, as the dye, a dye containing a polycyclic compound is adopted. The polycyclic compound includes a polycyclic hydrocarbon compound and a polycyclic heterocyclic compound. Further, the polycyclic compound may be a condensed polycyclic compound. Examples of the dye containing a polycyclic hydrocarbon compound include a naphthalene-based dye. Examples of the dye containing a polycyclic heterocyclic compound include a phenothiazine-based dye and an indole-based dye. In a more preferred embodiment, as the dye, at least one compound selected from the group consisting of indigo carmine, methylene blue, congo red, evans blue, and toluidine blue is adopted. In a further more preferred embodiment, as the dye, at least one compound selected from the group consisting of indigo carmine and methylene blue is adopted.

An addition amount of the dye is not particularly limited as long as the object of the present invention is achieved. For example, the addition amount of the dye can be less than 0.1% (w/v), 0.05% (w/v) or less, 0.02% (w/v) or less, 0.008% (w/v) or less, 0.007% (w/v) or less, 0.006% (w/v) or less, 0.005% (w/v) or less, 0.004% (w/v) or less, 0.003% (w/v) or less, 0.002% (w/v) or less, 0.001% (w/v) or less, or less than 0.001% (w/v) with respect to the total amount of the submucosal injection material. The addition amount of the dye can be, for example, 0.0001% (w/v) or more or 0.002% (w/v) or more with respect to the total amount of the submucosal injection material. From the viewpoint of balance between viscosity and noticeability, in one preferred embodiment, the addition amount of the dye in the submucosal, injection material is 0.008% (w/v) or less and 0.0001% (w/v) or more. In a more preferred embodiment, the addition amount of the dye in the submucosal injection material is 0.0001% (w/v) or more and 0.005% (w/v) or less.

In a further more preferred embodiment, the addition amount of the dye in the submucosal injection material is 0.0001% (w/v) or more and 0.002% (w/v) or less.

In one embodiment, the dye is added in such an amount that the storage stability of the submucosal injection material is improved as compared with a comparative injection material (control, hereinafter the same shall apply) which contains hyaluronic acid but does not contain the dye.

In one embodiment, the dye is added in such an amount that shortening of the shelf life of the submucosal injection material is prevented as compared with a comparative injection material which contains hyaluronic acid but does not contain the dye.

In one embodiment, the dye is added in such an amount that the viscosity of the submucosal injection material is enhanced as compared with a comparative injection material which contains hyaluronic acid but does not contain the dye.

In one embodiment, the dye is added in such an amount that formation of insoluble microparticles of the submucosal injection material is prevented as compared with a comparative injection material which contains hyaluronic acid but does not contain the dye.

The viscosity of the submucosal injection material is important from the viewpoint of swelling or elevation of the mucosal lesion site. In one embodiment, the dye is added in such an amount that reduction of the viscosity of the submucosal injection material when the material is stored at 40° C. is prevented as compared with a comparative injection material which contains hyaluronic acid but does not contain the dye. The storage period can be, for example, 7 days, 14 days, or 30 days. For the details of the storage conditions, the description of Examples is referred to.

In one embodiment, the dye is added in such an amount that a viscosity reduction ratio of the submucosal injection material when the material is stored at 40° C. for 30 days is 5.0% or less. In a preferred embodiment, the dye is added in such an amount that a viscosity reduction ratio when the submucosal injection material is stored at 40° C. for 30 days is 3.0% or less. In a more preferred embodiment, the dye is added in such an amount that a viscosity reduction ratio when the submucosal injection material is stored at 40° C. for 30 days is 2.5% or less. In a further more preferred embodiment, the dye is added in such an amount that a viscosity reduction ratio when the submucosal injection material is stored at 40° C. for 30 days is 2.0% or less. Note that in the present description, the "viscosity reduction ratio" is measured by the method described in Examples.

In one embodiment, the submucosal injection material has an absorbance residual ratio of 85% or more when the material is stored at 40° C. for 30 days. In a preferred embodiment, the submucosal injection material has an absorbance residual ratio of 95% or more when the material is stored at 40° C. for 30 days. In a more preferred embodiment, the submucosal injection material has an absorbance residual ratio of 99% or more when the material is stored at 40° C. for 30 days. Note that in the present description, the "absorbance residual ratio" is measured by the method described in Examples.

The number of insoluble microparticles in the submucosal injection material can affect the operability at the time of injection. In one embodiment, the dye is added in such an amount that the rate of increase in the number of insoluble microparticles having a diameter of 10 μm or more between before and after a photostability testing is 6.0 times or less, 5.5 times or less, 5.0 times or less, 4.5 times or less, 4.0 times or less, 3.5 times or less, 3.0 times or less, 2.5 times or less, 2.0 times or less, 1.5 times or less, or 1.0 times or less. In one embodiment, the dye is added in such an amount that the rate of increase in the number of insoluble microparticles having a diameter of 25 nm or more between before and after a photostability testing is 13.0 times or less, 12.0 times or less, 11.0 times or less, 10.0 times or less, 9.0 times or less, 3.0 times or less, 7.0 times or less, 6.0 times or less, 5.0 times or less, 4.0 times or less, 3.0 times or less, 2.0 times or less, or 1.0 times or less. Note that the rate of increase in the number of insoluble microparticles is a value representing the number of insoluble microparticles after a photostability testing by a proportion with respect, to the number of insoluble microparticles before exposure to light. The photostability testing is carried out by sealing the submucosal injection material in a transparent glass vial and then exposing the material to light under the conditions that the total illuminance is 1,200,000 lux·hr (2,000 lux×25 days), the total near-ultraviolet radiation energy is 317 W·h/m$^2$ and at 25° C. In one embodiment, when the submucosal injection material is stored at 5° C. for 25 days under a light-shielded condition, the number of insoluble microparticles having a diameter of 25 μm or more present in 20 mL of the submucosal injection material is 30 or less. In a preferred embodiment, when the submucosal injection material is stored at 5° C. for 25 days under a light-shielded condition, the number of insoluble microparticles having a diameter of 25 μm or more present in 20 mL of the submucosal injection material is 20 or less. In a more preferred embodiment, when the submucosal injection material is stored at 5° C. for 25 days under a light-shielded condition, the number of insoluble microparticles having a diameter of 25 μm or more present in 20 mL of the submucosal injection material is 15 or less. The number of insoluble microparticles is measured according to the insoluble microparticle test method for injections described in the Japanese Pharmacopoeia 17th Edition.

For example, when indigo carmine is used as the dye, the addition amount in the submucosal injection material can be, for example, 0.004% (w/v) or less, 0.003% (w/v) or less, 0.002% (w/v) or less, or 0.001% (w/v) or loss. The addition amount of indigo carmine in the submucosal injection material can be, for example, 0.0001% (w/v) or more or 0.0002% (w/v) or more. From the viewpoint of balance between viscosity and noticeability, in a preferred embodiment, the addition amount of indigo carmine in the submucosal injection material is 0.0001% (w/v) or more and 0.004% (w/v) or less. In a more preferred embodiment, the addition amount of indigo carmine in the submucosal injection material is 0.0002% (w/v) or more and 0.003% (w/v) or less.

For example, when methylene blue is used as the dye, the addition amount in the submucosal injection material can be, for example, 0.008% (w/v) or less, 0.007% (w/v) or less, 0.006% (w/v) or less, 0.005% (w/v) or less, 0.004% (w/v) or less, 0.003% (w/v) or less, 0.002% (w/v) or less, 0.001% (w/v) or less, or less than 0.001% (w/v). The addition amount of methylene blue in the submucosal injection material can be, for example, 0.0001% (w/v) or more or 0.0002% (w/v) or more. From the viewpoint of balance between viscosity and noticeability, in a preferred embodiment, the addition amount of methylene blue in the submucosal injection material is 0.008% (w/v) or less and 0.0001% (w/v) or more. In a more preferred embodiment, the addition amount of methylene blue in the submucosal injection material is 0.0001% (w/v) or more and 0.008% (w/v) or less. In a further more preferred embodiment, the addition amount of methylene blue in the submucosal injection material is 0.0001% (w/v) or more and 0.002% (w/v) or less.

One embodiment of the present invention relates to a method for improving the storage stability of a submucosal injection material containing hyaluronic acid. The method includes adding a dye to the submucosal injection material. The improvement of the storage stability of the submucosal injection material can be evaluated by comparing the quality characteristic with a comparative injection material which does not contain the dye that is contained in the submucosal injection material, and contains hyaluronic acid. In one embodiment, the quality characteristic is viscosity, and for example, a higher viscosity of the submucosal injection material relative to the viscosity of the comparative injection material is to serve as an index of improvement of the storage stability. In another embodiment, the quality characteristic is the number of insoluble microparticles, and for example, a smaller number of insoluble microparticles contained in the submucosal injection material relative to the number of insoluble microparticles contained in the comparative injection material is to serve as an index of improvement of the storage stability. The comparison may be performed after the submucosal injection material and the comparative injection material are stored for a predetermined period of time. In a further embodiment, the storage is performed under the conditions of 40° C. and 75% relative humidity (RH) for 30 days.

One embodiment of the present invention relates to a method for preventing color fading of a dye in a submucosal injection material containing hyaluronic acid and the dye, or a method for improving an absorbance residual ratio.

In the present description, the "addition" of the dye is not particularly limited as long as it is an operation to mix hyaluronic acid and the dye. For example, the dye may be added to hyaluronic acid, or hyaluronic acid may be added to the dye. Further, the dye itself may be added, or may be added as a dye solution (for example, a dye aqueous solution).

One embodiment of the present invention relates to a method for preventing shortening of the shelf life of a submucosal injection material containing hyaluronic acid. The method includes adding a dye to the submucosal injection material. The prevention of shortening of the shelf life of a submucosal injection material means that the product shelf life of the submucosal injection material is equivalent or longer, as compared with the product shelf life of a comparative injection material which does not contain the dye that is contained in the submucosal injection material, and contains hyaluronic acid. For example, the prevention of shortening of the shelf life of the submucosal injection material may be determined to be achieved when a viscosity reduction ratio in the storage period is smaller as compared with a comparative injection material which does not contain the dye that is contained in the submucosal injection material, and contains hyaluronic acid as a control. The shelf life (also referred to as service life) of the submucosal injection material can be set by a person skilled in the art in consideration of a relationship between a storage period and quality retention (for example, reduction of viscosity) or technical knowledge of EMR or ESD. The shelf life of the submucosal injection material can be, for example, 2 years or more, 2 years and 6 months or more, 3 years or more, and 3 years and 6 months or more from the date of production. The upper limit of the shelf life is not particularly limited, but may be, for example, 5 years or less.

One embodiment of the present invention relates to a method for enhancing the viscosity of a submucosal injection material containing hyaluronic acid. The method includes adding a dye to hyaluronic acid. The enhancement of the viscosity of a submucosal injection material can be evaluated by comparison with the viscosity of a comparative injection material which does not contain the dye that is contained in the submucosal injection material, and contains hyaluronic acid. For example, when the submucosal injection material shows a viscosity equal to or more than that of the comparative injection material, and shows a swelling property suitable for or ESD, the viscosity can be determined to be enhanced. Alternatively, when the submucosal injection material shows a higher viscosity than that of the comparative injection material, the viscosity can be determined to be enhanced. The comparison can be carried out after the submucosal injection material and the comparative injection material are stored for a predetermined period of time. In a further embodiment, the storage is performed under the conditions of 40° C. and 75% RH for 30 days.

The submucosal injection material may contain an additive such as a stabilizer, an emulsifier, an osmotic pressure-controlling agency, a buffer, a tonicity agent, a preservative, a soothing agent, an excipient, a binder, a lubricant, or a disintegrant to such an extent that the object of the present invention is not impaired. In a preferred embodiment, the submucosal injection material contains a physiological phosphate buffered solution (sodium chloride, sodium hydrogen phosphate, and sodium dihydrogen phosphate). In one embodiment, the content of sodium chloride may be 0.5% (w/v) or more and 2% (w/v) or less.

In a preferred embodiment, the submucosal injection material need not contain epinephrine.

The pH of the submucosal injection material is not particularly limited. In one embodiment, the pH of the submucosal injection material may be 7 or more and 8 or less.

The osmotic pressure ratio (the ratio with respect to saline) of the submucosal injection material is also not particularly limited. In one embodiment, the osmotic pressure ratio of the submucosal injection material may be 0.9 or more and 1.2 or less.

In one embodiment, the submucosal injection material may be in a liquid state or a gel state. In a further embodiment, the submucosal Injection material is a water-based solution (for example, an aqueous solution).

The submucosal injection material can be provided, for example, in the form of being enclosed in a vial or an injection syringe. The submucosal injection material may also be a sterilized one.

One aspect of the present invention relates to an endoscopic mucosal resection method or an endoscopic submucosal dissection method including injecting a submucosal injection material whose quality deterioration is prevented by the above-mentioned method into a submucosa of a patient to form an elevation of a mucosal layer. As the mucosa, a digestive mucosa (for example, a gastric mucosa, a large intestine mucosa, an esophageal mucosa, or the like) is exemplified. In a further embodiment, the submucosal injection material is injected at a tumor site.

Hereinafter, specific embodiments of the present invention will be illustrated, however, the invention is not limited thereto.

[1] A method for improving the storage stability of a submucosal injection material containing hyaluronic acid, including adding a dye to the submucosal injection material.

[2] The method according to [1], wherein the dye is added in such an amount that the storage stability of the submucosal injection material is improved as compared with a comparative injection material which contains hyaluronic acid but does not contain the dye.

[3] The method according to [1] or [2], wherein the dye is added in such an amount that reduction of the viscosity of the submucosal injection material when the material is stored at 40° C. for 30 days is prevented as compared with a comparative injection material which contains hyaluronic acid but does not contain the dye.

[4] The method according to any one of [1] to [3], wherein the dye is added in such an amount that a viscosity reduction ratio when the submucosal injection material is stored at 40° C. for 30 days is 3.0% or less.

[5] The method according to any one of [1] to [4], wherein the dye includes at least one type selected from the group consisting of indigo carmine, methylene blue, congo red, evans blue, and toluidine blue.

[6] The method according to any one of [1] to [5], wherein the submucosal injection material does not contain epinephrine.

[7] An endoscopic mucosal resection method or an endoscopic submucosal dissection method, including injecting a submucosal injection material having storage stability improved by the method according to any one of [1] to [6] into a submucosa of a patient who needs the submucosal injection material so as to form an elevation of a mucosal layer.

[8] The method according to [7], wherein the mucosal layer is selected from the group consisting of esophagus, stomach, and large intestine.

[9] The method according to [7] or [8], wherein the submucosal injection material is injected at a tumor site.

[10] A method for preventing shortening of the shelf life of a submucosal injection material containing hyaluronic acid, including adding a dye to the submucosal injection material.

[11] The method according to [10], wherein the dye is added in such an amount that shortening of the shelf life of the submucosal injection material is prevented as compared with a comparative injection material which contains hyaluronic acid but does not contain the dye.

[12] The method according to [10] or [11], wherein the dye is added in such an amount that, reduction of the viscosity of the submucosal injection material when the material is stored at 40° C. for 30 days is prevented as compared with a comparative injection material which contains hyaluronic acid but does not contain the dye.

[13] The method according to any one of [10] to [12], wherein the dye is added in such an amount that a viscosity reduction ratio when the submucosal injection material is stored at 40° C. for 30 days is 3.0% or less.

[14] The method according to any one of [10] to [13], wherein the dye includes at least one type selected from the group consisting of indigo carmine, methylene blue, congo red, evans blue, and toluidine blue.

[15] The method according to any one of [10] to [14], wherein the submucosal injection material does not contain epinephrine.

[16] An endoscopic mucosal resection method or an endoscopic submucosal dissection method, including injecting a submucosal injection material whose shelf life is prevented from shortening by the method according to any one of [10] to [15] into a submucosa of a patient who needs the submucosal injection material so as to form an elevation of a mucosal layer.

[17] The method according to [16], wherein the mucosal layer is selected from the group consisting of esophagus, stomach, and large intestine.

[18] The method according to [16] or [17], wherein the submucosal injection material is injected at a tumor site.

[19] A submucosal injection material, containing hyaluronic acid and a dye, wherein a viscosity reduction ratio of the material when the material is stored at 40° C. for 30 days is 5% or less.

[20] The submucosal injection material according to [19], wherein the dye includes at least one type selected from the group consisting of indigo carmine, methylene blue, congo red, evans blue, and toluidine blue.

[21] The submucosal injection material according to [19] or [20], wherein the content of the dye is 0.02% (w/v) or less.

[22] The submucosal injection material according to any one of [19] to [21], which contains 0.5% (w/v) or more and 2% (w/v) or less of sodium chloride.

[23] The submucosal injection material according to any one of [19] to [22], which is in a liquid state or a gel state.

[24] The submucosal injection material according to any one of [19] to [23], which does not contain epinephrine.

[25] The submucosal injection material according to any one of [19] to [24], wherein the content of hyaluronic acid is 0.1% (w/v) or more and 0.5% (w/v) or less.

[26] An endoscopic mucosal resection method or an endoscopic submucosal dissection method, including injecting the submucosal injection material according to any one of [19] to [25] into a submucosa of a patient so as to form an elevation of a mucosal layer.

[27] The method according to [26], wherein the mucosal layer is selected from the group consisting of esophagus, stomach, and large intestine.

[28] The method according to [26] or [27], wherein the submucosal injection material is injected at a tumor site.

[29] A method for producing a submucosal injection material whose viscosity reduction is prevented, including preparing a composition containing hyaluronic acid and a dye, wherein a viscosity reduction ratio of the material when the submucosal injection material is stored at 4° C. for 30 days is 5% or less.

The submucosal injection material and the like are described as examples, however, those in which the "submucosal injection material" and the "comparative injection material (control)" in the present description are replaced with a "composition" and a "composition (control)" are also included in the idea of the present invention.

EXAMPLES

Hereinafter, preferred embodiments of the present invention will be described in more detail with reference to Examples, but the technical scope of the present invention is not limited to the following Examples.

Example 1

80 mg of sodium hyaluronate (weight average molecular weight: about 800,000), 180 mg of sodium chloride, and a dye in an amount to give the final concentration shown in Table 1 were dissolved in 20 mL of a phosphate buffer solution, whereby a submucosal injection material was obtained (pH 7.5). Note that a submucosal injection material prepared by dissolving 80 mg of sodium hyaluronate and 180 mg of sodium chloride in 20 mL of a phosphate buffer solution was used as a comparative injection material (control).

The obtained submucosal injection material was sealed into a glass vial and stored in a constant temperature and humidity chamber at 40° C. and 75% RH, and the viscosity and noticeability were evaluated over time.

(Measurement of Viscosity)

The intrinsic viscosity (dL/g) of the submucosal injection material was measured by the following method. That is, a material obtained by diluting the submucosal injection material with distilled water to 10% (w/v) was used as a test solution, and 10 mL of the test solution was placed in an Ubbelohde viscometer, and measurement was performed in a constant temperature chamber at 30° C. using an automatic kinematic viscosity tester (manufactured by RIGO, Co., Ltd., model: VMC-252).

Note that the viscosity reduction ratio in Table 1 was determined by the following formula (I).

$$\text{Viscosity reduction ratio (\%)} = [(V_0 - V_t)/V_0] \times 100 \qquad \text{Formula (I)}$$

$V_0$: Intrinsic viscosity before starting storage
$V_t$: Intrinsic viscosity after storage for arbitrary period
(Evaluation of Coloration)

The coloration was evaluated by visual observation.

TABLE 1

| | | Viscosity reduction ratio (%) | | |
| --- | --- | --- | --- | --- |
| Storage period | | 7 days | 14 days | 30 days |
| Comparative injection material (shelf life: 3.5 years) | | 1.9 | 1.9 | 3.1 |
| indigo carmine | 0.001% (w/v) | 0.0 | 0.7 | 2.0 |
| | 0.005% (w/v) | 4.7 | 13.3 | 23.3 |
| methylene blue | 0.001% (w/v) | −5.3 | 1.3 | 2.0 |
| | 0.005% (w/v) | 0.7 | 1.3 | 2.0 |

In the submucosal injection material containing methylene blue, no reduction in coloration (color fading) was observed throughout the storage period. In the submucosal injection material containing indigo carmine, the coloration was slightly reduced 30 days after starting storage.

Example 2

Submucosal injection materials were obtained by the same preparation method as in Example 1 using congo red, evans blue, and toluidine blue, respectively. The concentration of the dye was set to 0.001% (w/v) in each case.

The obtained submucosal injection material was sealed into a glass vial and stored in a constant temperature and humidity chamber at 40° C. and 75% RH for 30 days, and the viscosity reduction ratio before storage and after storage for 30 days was evaluated by the same measurement method as in Example 1.

The results are shown in Table 2.

TABLE 2

| Dye name | Viscosity reduction ratio (%) |
| --- | --- |
| congo red | −1.3 |
| evans blue | 0.5 |
| toluidine blue | 1.3 |

Example 3

Submucosal injection materials were obtained by the same preparation method as in Example 1 using dyes shown in Table 3, respectively. The concentration of the dye was set to 0.001% (w/v) in each case. The obtained submucosal injection material was sealed into a glass vial and stored in a constant temperature and humidity chamber at 40° C. and 75% RH, and the absorbance before storage and after storage for 30 days was evaluated.

(Measurement of Absorbance)

The absorbance of the submucosal injection material was measured to evaluate the color fading by the following method. First, a 0.001% (w/v) aqueous solution of each dye was prepared with distilled water, which was used as a test solution. The UV-Vis spectrum of the test solution was measured. The wavelength at which the measurement was performed was set to 350 nm or more and 800 nm or less. The wavelength at which the maximum absorption was exhibited within the measured range was defined as the measurement wavelength.

The absorbance of the submucosal injection material was measured at the measurement wavelength of each dye determined above.

Note that the absorbance residual ratio in Table 3 was determined by the following formula (II).

$$\text{Absorbance residual ratio (\%)} = Abs_{30}/Abs_0 \times 100 \quad \text{Formula (II)}$$

$Abs_0$: absorbance before starting storage
$Abs_{30}$: absorbance after storage for 30 days
The results are shown in Table 3.

TABLE 3

| Dye name | Measurement wavelength (nm) | Absorbance residual ratio (%) |
|---|---|---|
| congo red | 498.0 | 99.2 |
| evans blue | 608.0 | 99.1 |
| toluidine blue | 529.0 | 96.0 |
| indigo carmine | 611.5 | 87.2 |
| methylene blue | 664.5 | 99.4 |

Example 4

Submucosal Injection materials in which a dye and the concentration of the dye are as shown in Table 4 were obtained by the same preparation method as in Example 1 (pH 7.5). Further, a comparative injection material (control) was obtained by the same preparation method as in Example 1.

Each of the obtained submucosal injection materials and comparative injection material was sealed into a glass vial, and stored at 5° C. under a light-shielded condition for 25 days. The insoluble microparticles of the submucosal injection materials and the comparative injection material after storage for 25 days were evaluated.

(Measurement of Insoluble Microparticles)

The insoluble microparticles of the submucosal injection materials and the comparative injection material were measured by the following method. That is, the number of microparticles (having a diameter of 25 m or more) per 20 mL of a sample was measured by a light obscuration automatic particle counter (manufactured by Rion Co., Ltd.). The results are shown in Table 4.

TABLE 4

| | | Number of insoluble microparticles (particles/20 mL of sample) |
|---|---|---|
| Comparative injection material | | 51 |
| indigo carmine | 0.001% (w/v) | 9 |
| | 0.005% (w/v) | 9 |

TABLE 4-continued

| | | Number of insoluble microparticles (particles/20 mL of sample) |
|---|---|---|
| methylene blue | 0.001% (w/v) | 11 |
| | 0.005% (w/v) | 17 |

The invention claimed is:

1. A method for improving the storage stability of a submucosal injection material comprising hyaluronic acid, comprising adding a dye to the submucosal injection material,
   wherein the dye is indigo carmine, and
   an added amount of the indigo carmine is 0.004% (w/v) or less.

2. The method according to claim 1, wherein the dye is added in such an amount that the storage stability of the submucosal injection material is improved as compared with a comparative injection material which comprises hyaluronic acid but does not contain the dye.

3. A method for endoscopic mucosal resection or an endoscopic submucosal dissection, comprising:
   injecting the submucosal injection material having storage stability improved by the method according to claim 1 into a submucosa of a patient so as to form an elevation of a mucosal layer.

4. The method according to claim 3, wherein the submucosal injection material is injected at a tumor site.

5. A method for preventing shortening of the shelf life of a submucosal injection material containing hyaluronic acid, comprising adding a dye to the submucosal injection material,
   wherein the dye is indigo carmine,
   and an added amount of the indigo carmine is 0.004% (w/v) or less.

6. The method according to claim 5, wherein the dye is added in such an amount that shortening of the shelf life of the submucosal injection material is prevented as compared with a comparative injection material which contains hyaluronic acid but does not contain the dye.

7. A method for endoscopic mucosal resection or an endoscopic submucosal dissection, comprising:
   injecting the submucosal injection material of which shelf life is prevented from shortening by the method according to claim 5 into a submucosa of a patient so as to form an elevation of a mucosal layer.

8. The method according to claim 7, wherein the submucosal injection material is injected at a tumor site.

9. A method for improving the storage stability of a submucosal injection material comprising hyaluronic acid, comprising adding a dye to the submucosal injection material,
   wherein the dye is selected from the group consisting of methylene blue, congo red, evans blue, and toluidine blue, and
   an added amount of the dye is 0.005% (w/v) or less.

10. The method according to claim 9, wherein the dye is added in such an amount that the storage stability of the submucosal injection material is improved as compared with a comparative injection material which comprises hyaluronic acid but does not contain the dye.

11. A method for endoscopic mucosal resection or an endoscopic submucosal dissection, comprising:
   injecting the submucosal injection material having storage stability improved by the method according to claim 9 into a submucosa of a patient so as to form an elevation of a mucosal layer.

12. The method according to claim 11, wherein the submucosal injection material is injected at a tumor site.

13. A method for preventing shortening of the shelf life of a submucosal injection material containing hyaluronic acid, comprising adding a dye to the submucosal injection material,
   wherein the dye is selected from the group consisting of methylene blue, congo red, evans blue, and toluidine blue, and
   an added amount of the dye is 0.005% (w/v) or less.

14. The method according to claim 13, wherein the dye is added in such an amount that shortening of the shelf life of the submucosal injection material is prevented as compared with a comparative injection material which contains hyaluronic acid but does not contain the dye.

15. A method for endoscopic mucosal resection or an endoscopic submucosal dissection, comprising:
   injecting the submucosal injection material of which shelf life is prevented from shortening by the method according to claim 13 into a submucosa of a patient so as to form an elevation of a mucosal layer.

16. The method according to claim 15, wherein the submucosal injection material is injected at a tumor site.

* * * * *